United States Patent
Kauphusman et al.

(10) Patent No.: US 10,675,444 B2
(45) Date of Patent: Jun. 9, 2020

(54) DEVICE FOR REDUCING AXIAL SHORTENING OF CATHETER OR SHEATH DUE TO REPEATED DEFLECTION

(71) Applicant: St. Jude Medical, Atrial Fibrillation Division, Inc., St. Paul, MN (US)

(72) Inventors: James V. Kauphusman, Champlin, MN (US); Allan M. Fuentes, Mound, MN (US); Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 111 days.

(21) Appl. No.: 15/342,539

(22) Filed: Nov. 3, 2016

(65) Prior Publication Data
US 2017/0136213 A1 May 18, 2017

Related U.S. Application Data

(63) Continuation of application No. 13/764,294, filed on Feb. 11, 2013, now Pat. No. 9,486,612, which is a
(Continued)

(51) Int. Cl.
*A61M 25/01* (2006.01)
*A61M 25/00* (2006.01)

(52) U.S. Cl.
CPC ...... *A61M 25/0147* (2013.01); *A61M 25/005* (2013.01); *A61M 25/0012* (2013.01);
(Continued)

(58) Field of Classification Search
CPC ............ A61M 25/0043; A61M 25/005; A61M 25/0053; A61M 25/0054; A61M 25/0067;
(Continued)

(56) References Cited

U.S. PATENT DOCUMENTS 4,580,551 A 4/1986 Siegmund et al.
4,753,223 A * 6/1988 Bremer ................ A61B 1/0058
600/140
(Continued)

FOREIGN PATENT DOCUMENTS

CN 101321552 12/2008
CN 101443068 5/2009
(Continued)

OTHER PUBLICATIONS

Extended European Search Report, App. No. EP 10 82 8716 dated Apr. 19, 2013.
(Continued)

*Primary Examiner* — Quynh-Nhu H. Vu
(74) *Attorney, Agent, or Firm* — Dykema Gossett PLLC

(57) ABSTRACT

A deflectable medical device incorporates a strut that is configured to reduce or eliminate axial shortening of the deflectable portion of the medical device, for example, the deflectable distal end portion of a catheter or access sheath. The strut may is coaxially disposed in the medical device in the section that is contemplated to undergo the repeated deflection. The strut provides improved column strength and axial restoration. The strut may be stent-like device, an elongate device having opposing ends coupled by a connecting lattice involving a plurality of helical connecting elements or a tube having a plurality of circumferentially-extending slots arranged in longitudinally-extending rows.

22 Claims, 8 Drawing Sheets

Related U.S. Application Data continuation of application No. 12/615,016, filed on Nov. 9, 2009, now Pat. No. 8,376,991.

(52) U.S. Cl.
CPC .... *A61M 25/0051* (2013.01); *A61M 25/0133* (2013.01); *Y10T 29/49826* (2015.01)

(58) Field of Classification Search
CPC ............ A61M 25/0068; A61M 25/008; A61M 25/0138; A61M 25/0144; A61M 25/0147
See application file for complete search history.

(56) References Cited

U.S. PATENT DOCUMENTS

| | | | |
|---|---|---|---|
| 4,846,573 A | | 7/1989 | Taylor |
| 5,002,041 A | * | 3/1991 | Chikama .............. A61B 1/0055 600/139 |
| 5,058,568 A | | 10/1991 | Irion |
| 5,176,126 A | * | 1/1993 | Chikama .............. A61B 1/0055 138/120 |
| 5,179,935 A | | 1/1993 | Miyagi |
| 5,325,845 A | | 7/1994 | Adair |
| 5,329,923 A | | 7/1994 | Lundquist |
| 5,381,782 A | | 1/1995 | de la Rama et al. |
| 5,676,653 A | | 10/1997 | Taylor et al. |
| 5,681,263 A | | 10/1997 | Flesch |
| 5,827,242 A | | 10/1998 | Follmer et al. |
| 6,033,394 A | | 3/2000 | Vidlund et al. |
| 6,213,995 B1 | | 4/2001 | Steen et al. |
| 6,270,453 B1 | * | 8/2001 | Sakai .................. A61B 1/0055 600/141 |
| 6,273,880 B1 | | 8/2001 | Berg et al. |
| 6,530,897 B2 | | 3/2003 | Nardeo |
| 6,585,718 B2 | | 7/2003 | Hayzelden et al. |
| 6,749,560 B1 | * | 6/2004 | Konstorum ........ A61B 1/00071 600/139 |
| 7,276,064 B2 | | 10/2007 | Paul |
| 7,422,579 B2 | | 9/2008 | Wahr et al. |
| 8,376,991 B2 | * | 2/2013 | Kauphusman .... A61M 25/0012 600/137 |
| 9,486,612 B2 | * | 11/2016 | Kauphusman .... A61M 25/0012 |
| 2002/0082585 A1 | | 6/2002 | Carroll et al. |
| 2002/0165461 A1 | | 11/2002 | Hayzelden et al. |
| 2003/0191451 A1 | | 10/2003 | Gilmartin |
| 2004/0087932 A1 | | 5/2004 | Lawrence et al. |
| 2004/0143197 A1 | | 7/2004 | Soukup et al. |
| 2005/0070844 A1 | | 3/2005 | Chow et al. |
| 2006/0184106 A1 | | 8/2006 | McDaniel et al. |
| 2006/0241564 A1 | | 10/2006 | Corcoran et al. |
| 2007/0021737 A1 | | 1/2007 | Lee |
| 2007/0167876 A1 | | 7/2007 | Euteneuer et al. |
| 2007/0179486 A1 | | 8/2007 | Welch |
| 2007/0225562 A1 | | 9/2007 | Spivey |
| 2008/0091169 A1 | | 4/2008 | Heideman et al. |
| 2008/0091193 A1 | | 4/2008 | Kauphusman et al. |
| 2008/0097398 A1 | * | 4/2008 | Mitelberg ......... A61M 25/0043 604/525 |
| 2008/0161762 A1 | | 7/2008 | Stehr et al. |
| 2009/0024110 A1 | | 1/2009 | Heideman et al. |
| 2009/0209815 A1 | * | 8/2009 | Smith .................. A61B 1/0055 600/114 |
| 2009/0312698 A1 | * | 12/2009 | Farrell .............. A61M 25/0009 604/95.04 |
| 2009/0312699 A1 | * | 12/2009 | Pudelko ............ A61M 25/0147 604/95.04 |
| 2010/0312178 A1 | * | 12/2010 | Olsen ................ A61M 25/0133 604/95.04 |
| 2011/0218492 A1 | | 9/2011 | McDaniel et al. |

FOREIGN PATENT DOCUMENTS

| | | |
|---|---|---|
| JP | H03-073125 A | 3/1991 |
| JP | H11-509751 A | 8/1999 |
| JP | 2004-329254 A | 11/2004 |
| JP | 2006-255401 A | 9/2006 |
| WO | WO 1994/014494 | 7/1994 |
| WO | WO 1998/058696 | 12/1998 |
| WO | WO 2009/086007 | 7/2009 |

OTHER PUBLICATIONS

International Search Report and Written Opinion, App. No. PCT/US2010/049741 dated Nov. 15, 2010.

* cited by examiner

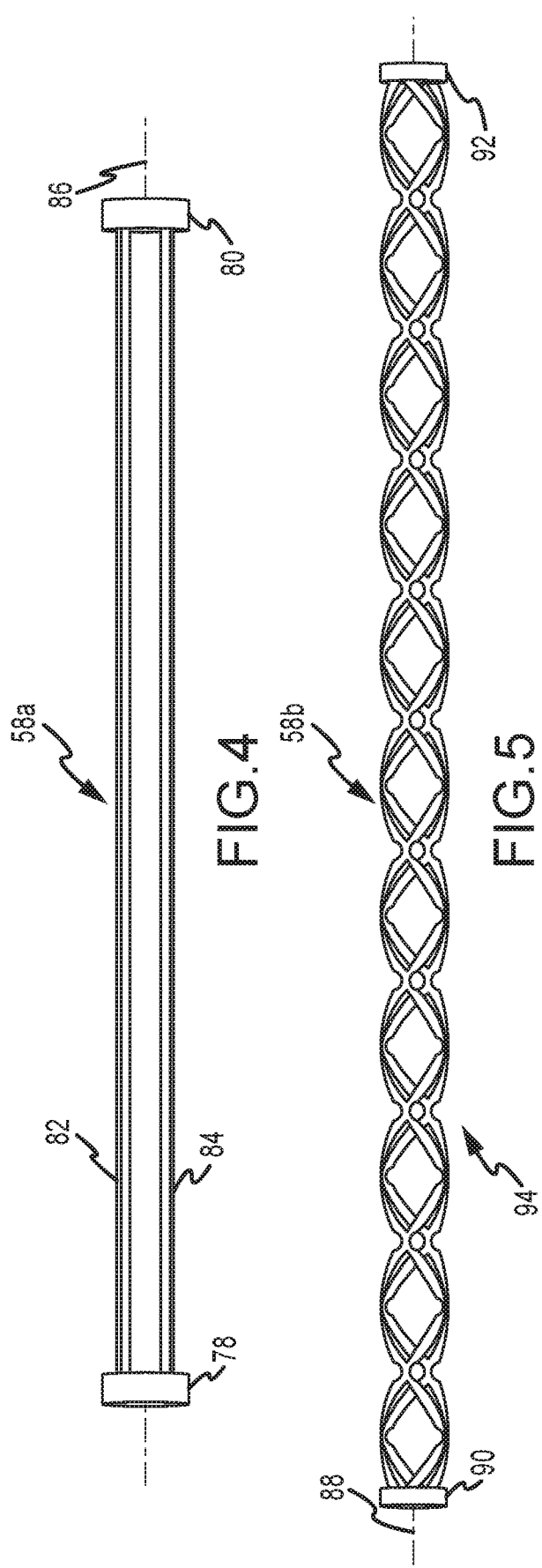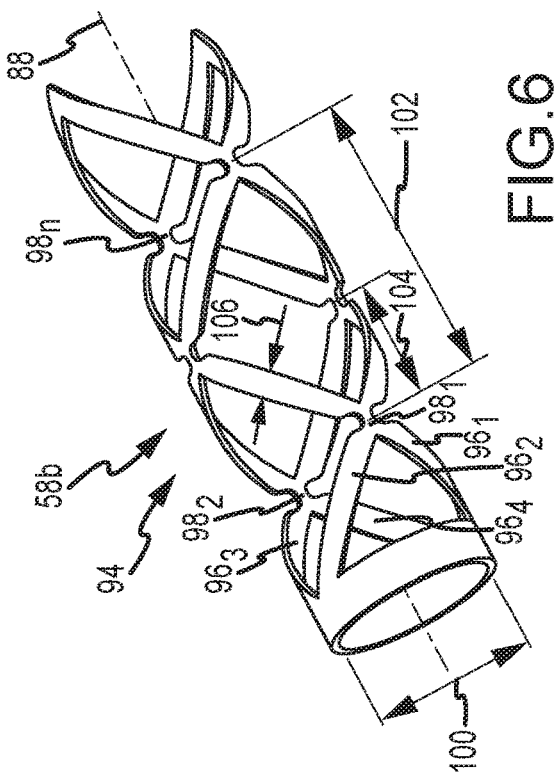

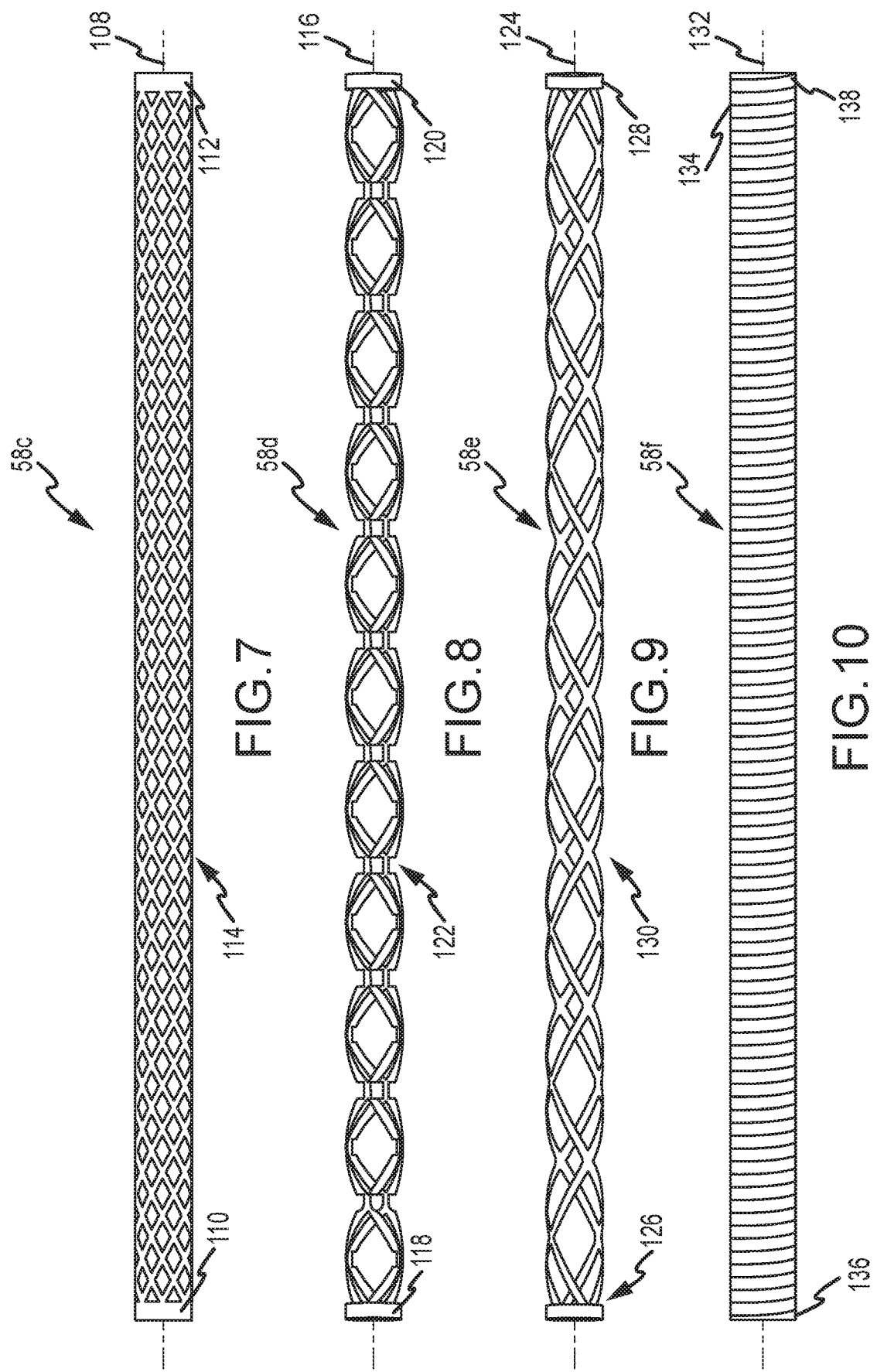

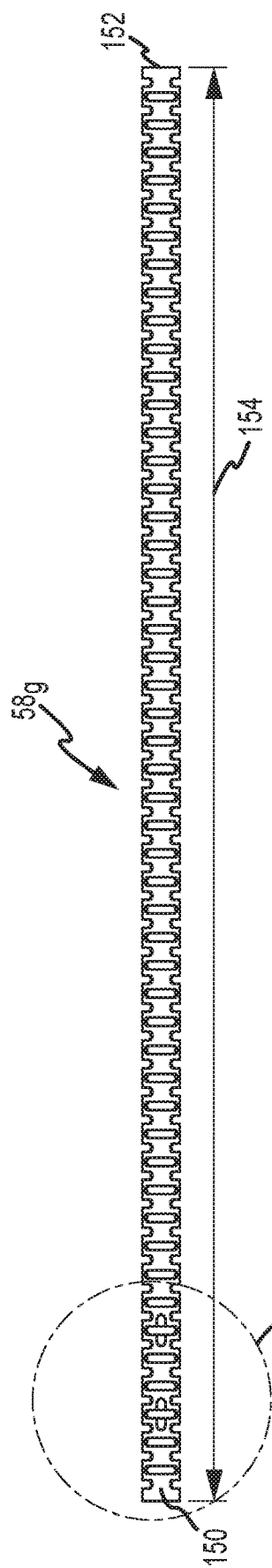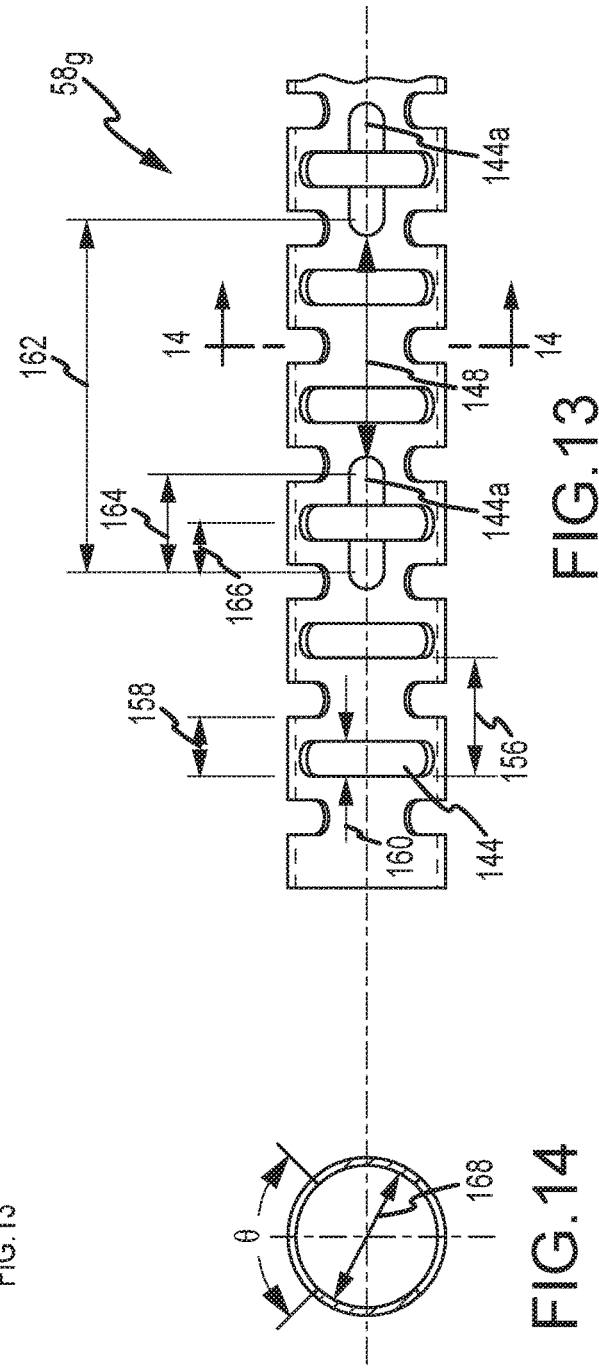
FIG. 12
FIG. 13
FIG. 14

DEVICE FOR REDUCING AXIAL SHORTENING OF CATHETER OR SHEATH DUE TO REPEATED DEFLECTION

CROSS-REFERENCE TO RELATED APPLICATIONS

This application is a continuation of U.S. application Ser. No. 13/764,294, filed 11 Feb. 2013 (the '294 application), now pending, which is a continuation of U.S. application Ser. No. 12/615,016, filed 9 Nov. 2009 (the '016 application), U.S. Pat. No. 8,376,991. The '294 application and the '016 application are both hereby incorporated by reference as though fully set forth herein.

BACKGROUND OF THE INVENTION a. Field of the Invention

The present disclosure relates to a device for reducing axial shortening due to repeated deflection of a catheter or catheter access device, such as an access sheath or introducer.

b. Background Art

Many medical procedures require the introduction of specialized medical devices into and/or around the human heart. In particular, there are a number of medical procedures that require the introduction of specialized devices including, but not limited to, catheters, dilators, and needles to areas, such as into the atria or ventricles to access the inner surface of the heart, or into the pericardial sac surrounding the heart to access the epicardial or outer surface of the heart. Catheters and access sheaths or introducers have been used for medical procedures for a number of years. It is typically necessary for introducers and catheters to exhibit a degree of flexibility to be able to maneuver through the vasculature of a patient during the performance of medical procedures. Accordingly, catheters and access sheaths often have deflectable sections located at the distal end portion thereof.

To facilitate deflection, conventional sheaths, introducers, and catheters are commonly configured with steering or pull wires to control the movement and relative curvature of the devices, particularly at the distal end portion. The pull wires typically extend along the length of the catheter or sheath and are coupled and/or connected to a control mechanism at the proximal end portion, such as, for example, a knob that can be rotated or to a robotic control system. In operation, the pull wires are used to "pull" on one side or the other side of the device to control deflection, for example, to deflect the distal end portion. These devices are conventionally made from PEBAX that must withstand the force applied to the pull wire so that the distal end portion bends.

After repeated deflections, however, the deflectable distal end becomes shortened in axial length (i.e., in a state of being compressed relative to the original axial length), particularly after the catheter or access sheath has been resident in the body for some time and is thus at or near body temperature. As a result of the reduced axial length, the catheter or sheath's access capabilities are reduced. An accomplished physical can make some manual adjustments to compensate for the "compressed" distal end (i.e., the loss of travel) but only up to a certain point beyond which the amount the distal end has been shortened is deemed excessive.

To better understand this phenomena, one may notice that in a conventional deflectable access sheath, the inner and outer diameters of the sheath wall may differ by as much as 0.50 inches (e.g., if one considers a 13 Fr. Device with a small curl of 180 degrees). This difference must be accommodated during deflections, which results in a series of compressions and extensions of the polymer material, resulting in the permanent axial shortening or compression described above. Moreover, as the number of deflections increase, the polymer material weakens (as does the braid, usually a part of the construction), begins to give way and eventually may fail. This failure is usually not catastrophic since as described above, a physician can recognize the reduction in available travel in the distal tip section and make adjustments. However, there are situations where the loss of travel may prevent particular areas of the anatomy from being accessed, such as the right superior pulmonary vein (RSPV) and right inferior pulmonary vein (RIPV).

In addition, recent advances in the robotic control of catheters, access sheaths and the like allow advancement, retraction and various deflections and/or steering to be controlled robotically. When the actuation mechanism to "pull" the pull wires is a robotic control system, the physician's ability to compensate for axial shortening described above is inapplicable. And while closed loop feedback systems may be configured to account for the loss of distal travel (i.e., to mimic what a physician would do), it is nonetheless desirable to minimize or eliminate the axial shortening of the deflectable distal end portion in order to provide sufficient control authority to the actuation mechanism as an initial matter.

It is known to include a wire mesh in an introducer catheter, as seen by reference to U.S. Patent Publication 2009/0024110 entitled CATHETER AND INTRODUCER CATHETER HAVING TORQUE TRANSFER LAYER AND METHOD OF MANUFACTURE to Heideman et al ("Heideman"), owned by the common assignee of the present invention, and hereby incorporated by reference in its entirety. Heideman disclose a torque transfer layer in the catheter, which includes a wire mesh, to provide increased strength, flexibility, and kink resistance. While the torque transfer layer provides an excellent platform to improve torque along a shaft, there is still a need for a mechanism to reduce or eliminate axial shortening of a catheter or sheath.

There is therefore a need to minimize or eliminate one or more of the problems as set forth above.

BRIEF SUMMARY OF THE INVENTION

One advantage of the methods and apparatus described, depicted and claimed herein involves the reduction or elimination of axial shortening in deflectable medical devices due to repeated deflections (e.g., catheters, access sheaths or introducers having deflectable portions, such as a deflectable distal end portion).

The present disclosure is directed to medical devices having an elongate core and a strut. The elongate core has a proximal end portion and a deflectable distal end portion. The strut is disposed outwardly of the core at or near the distal end portion and is configured to reduce axial shortening of the deflectable distal end portion of the core due to repeated deflection. Where the medical device is an access sheath, the core may comprise a liner having a relatively large central lumen. Where the medical device is a catheter, the core may comprise a catheter shaft.

The strut, in several embodiments, provides longitudinal support but is also configured to allow a measure of flexibility, allowing deflectable medical devices to continue to function as intended (i.e., deflect) without requiring undue deflection forces.

A preferred embodiment of the strut comprises a tube having a predetermined wall thickness with a plurality of apertures, such as slots, formed through the wall thickness. Each slot may be circumferentially-oriented, i.e., having a greater length in the circumferential direction on the tube than in the longitudinal direction. Moreover, the slots may be organized in longitudinally-extending rows of slots, with slots in adjacent rows being axially offset by a predetermined pitch spacing.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 4 is an isometric view of a first embodiment of a strut suitable for use in the medical device of FIG. 2.

FIG. 5 is an isometric view of a second embodiment of a strut suitable for use in the medical device of FIG. 2.

FIG. 6 is an enlarged view of a portion of the strut of FIG. 5, showing a plurality of helical connecting elements in greater detail.

FIG. 7 is an isometric view of a third embodiment of a strut suitable for use in the medical device of FIG. 2 having a greater number of helical connecting elements as compared to the embodiment of FIGS. 5-6.

FIG. 8 is an isometric view of a fourth embodiment of a strut suitable for use in the medical device of FIG. 2 having wider helical connecting elements as compared to the embodiment of FIGS. 5-6.

FIG. 9 is an isometric view of a fifth embodiment of a strut suitable for use in the medical device of FIG. 2 having narrower helical connecting elements as compared to the embodiment of FIGS. 5-6.

FIG. 10 is an isometric view of a sixth embodiment of a strut suitable for use in the medical device of FIG. 2 having a coiled structure.

FIG. 12 is a side view of the seventh embodiment of FIG. 11.

FIG. 13 is an enlarged side view of an encircled distal portion of the embodiment of FIG. 12.

FIG. 14 is a cross-sectional view of the strut of FIG. 13 taken substantially along lines 14-14.

DETAILED DESCRIPTION OF THE INVENTION

In general, the instant disclosure relates to methods and apparatus for reducing or eliminating axial shortening due to repeated deflection in deflectable catheters, access sheaths or introducers or other deflectable medical devices. As described in the Background, a problem with conventional deflectable medical devices involves an axial shortening of the deflectable portion (e.g., deflectable distal end portion) after repeated deflections due to, among other things, structural (plastic) deformation, particularly when the material is at normal human body temperatures (i.e., ~37° C.). Embodiments according to the invention involve disposing a strut into the structure of the medical device at or near the section contemplated to undergo the repeated deflection. The strut provides longitudinal (column) support while at the same time exhibits a measure of flexibility, thereby allowing the medical device reduce or eliminate axial shortening while functioning as intended (e.g., deflection by a predetermined amount, such as 180° or 270°, based on a "pull" force that does not exceed a desired, maximum pull force, such as 10 lbs.).

Figure 1B:
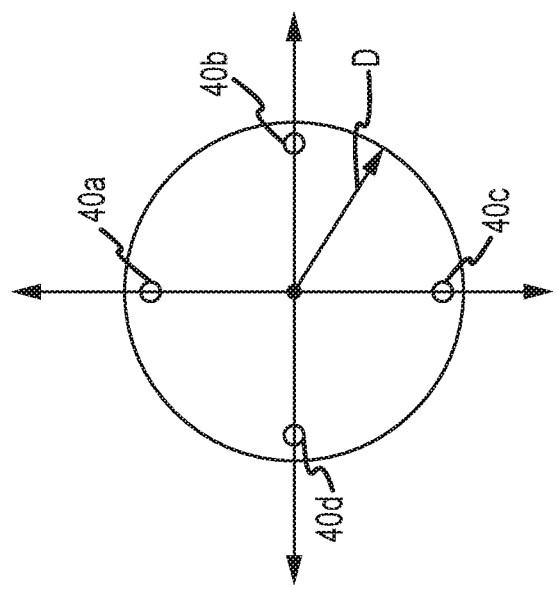
FIG. 1B is an axial cross-sectional view of the medical device of FIG. 1A that includes four steering wires.
Figure 1A:
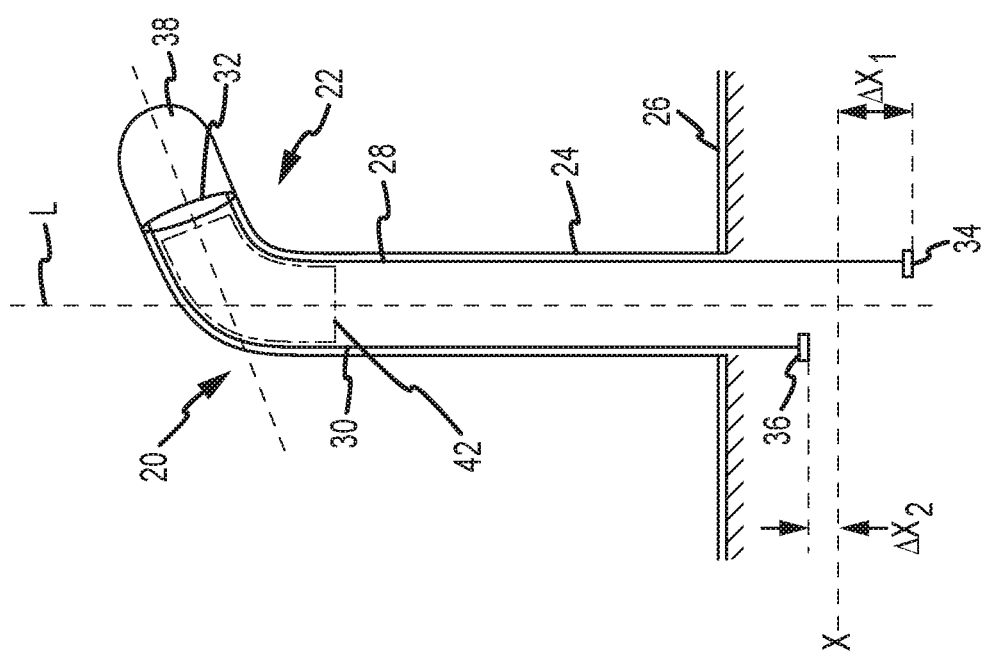
FIG. 1A is a side view of a deflectable medical device suitable for use in connection with embodiments of the invention.

FIG. 1A generally shows a deflectable medical device, such as a catheter 20, having a longitudinal axis L associated therewith, and further having a distal end portion 22 and a proximal end portion 24. It should be understood that the present invention may be useful to wide range of deflectable medical devices, including without limitation catheters and access sheaths, to name a few. Moreover, as described in the Background, the actuation of the pull or steering wires may be accomplished typically through the use of, for example, either a knob or the like that can be manually rotated by physician or alternatively, by a computer controlled robotic (e.g., articulated apparatus) control system having one or more degrees of mechanical freedom. The use of robotic devices to perform procedures and/or surgeries is increasing and devices provided herein (e.g., catheter or sheath) can be configured to be utilized in connection with various robotic applications. Nonetheless, without limitation or loss of generality, while FIGS. 1A-1B are described in connection with a robotic control system, it should be clearly understood that the embodiments of the present invention may be used with manually-actuated approaches as well as other ways now known or hereafter developed.

With continued reference to FIG. 1A, the proximal end portion 24 of the catheter 20 may be connected or attached to a support base 26. In a computer-controlled robotically actuated catheter control system, the support base 26 may be a portion of a disposable cartridge, and may be configured to interface with a robotic catheter manipulation assembly.

To enable deflection of the distal end portion 22, the catheter 20 may include a plurality of "pull" or steering wires, first and second steering wires 28, 30 being shown in FIG. 1A, as would be adequate for deflection in a single plane. The steering wires 28, 30 are each longitudinally situated within and along a substantial length of the catheter body. The steering wires 28, 30 may be formed of material having a high elastic modulus—such as, for example, steel or aluminum. The pull wires 28, 30 may also comprise fibrous materials (e.g., KEVLAR®) and can be push members. The catheter 20 may further include a pull or steering ring 32, which may take the form of a rigid ring firmly connected or affixed within a portion of the distal end portion 22. The catheter 20 may include additional pull or steering rings (i.e., anchors—not shown). Each steering wire may be connected to the pull ring 32. Alternatively, in embodiments having plural pull rings or anchors, the pull "wires" can couple to different locations on an anchor or to different anchors. The deflection mechanism may thus comprise construction techniques known in the art.

As generally depicted, proximal portions of the steering wires 28, 30 may be respectively connected to control members 34, 36. The catheter 20 may further include one or more electrodes, such as a tip electrode 38 as shown in FIG. 1A, that may be used for various diagnostic or therapeutic purposes, such as for detecting and mapping physical or electrical characteristics of cardiac tissue, or ablation, as known in the art.

When the catheter 20 is configured in an un-deflected state (not shown), the control members 34, 36 may both be situated at a one or more initial or common reference levels or datum (e.g., common datum X shown in FIG. 1A). The distal portion 22 may be deflected or displaced away from longitudinal axis L by selective actuation or tensioning of one or more of the steering wires. For example, the control member 34 may be translated in a proximal direction a distance $\Delta X_1$, which causes a tension response in the steering wire 28. The actuation of the steering wire 28 causes a corresponding rotation and deflection of the distal portion 22 in a direction toward the steering wire 28, as shown. While the control member 34 is actively deflected a distance $\Delta X_1$ in a first proximal direction, the control member 36 reactively moves or retracts a distance $\Delta X_2$ in a second, substantially opposing distal direction.

FIG. 1B is an axial cross-section view of a catheter embodiment that includes four steering wires 40a, 40b, 40c, 40d. Embodiments of the invention may be used in deflectable medical devices that deflect in two planes as well and the four steering wires are configured to facilitate such two plane deflection. In addition, the four steering wire arrangement may enable deflection in any radial direction (as described below) if so configured. While this illustration displays all steering wires spaced approximately 90 degrees apart, various other configurations may be provided. The respective tensioning of adjacent steering wires may cause a deflection of the distal portion 22 in a unique direction, e.g., direction D. Through selective actuation of pairs of steering wires, the distal portion 22 can be made to traverse circles of varying radii (i.e., depending on the amount of deflection of the tip away from axis L) as viewed from the top directly down on longitudinal axis L. The four-wire embodiment is similar to the two-steering wire embodiment since, when any wire or wires are tensioned ("pulled"), the remaining wires reactively move. Again, in alternative embodiments having plural pull rings or anchors, the pull "wires" can couple to different locations on an anchor or to different anchors. In a computer-controlled robotically-actuated catheter control system, a controller may be configured to translate the control element to achieve a desired catheter tip deflection.

It is not uncommon for deflectable medical devices to undergo repeated deflections of up to 180-270 degrees. These repeated deflections may occur after the medical device has been disposed in the patient's body for some time and is thus at or near body temperature. Moreover, for certain procedures, such as therapeutic treatment of atrial fibrillation, the medical devices may remain within the body for a number of hours on average. As a consequence, conventional deflectable medical devices exhibit a progressively increasing amount of axial shortening in the portion undergoing the repeated deflection, thereby reducing the available length/travel. The shortening creates the need for compensation by either a physician or a programmed robotic catheter control system.

To reduce or eliminate axial shortening, and in accordance with the invention, an axial shortening reducing means 42 (FIG. 1A) is disposed in and/or through that portion of the medical device that will undergo deflection. The means 42 is configured to reduce or eliminate the shortening of the axial length of that portion that might otherwise occur due to repeated deflection. The means 42 may take a plurality of different forms of a strut, as will be described and illustrated in connection with FIGS. 4-14. The means 42 provides column support and thus axial length restoration over repeated deflections while at the same time providing a measure of flexibility so as to allow the medical device to operate (i.e., deflect) as intended.

Before continuing with the detailed description, it should be understood that the embodiments to be described and illustrated herein are adapted for and thus will find usefulness in medical devices configured for deflection in any radial direction or even just two planes (e.g., see the four-wire catheter embodiment of FIG. 1B). However, embodiments of the invention are also useful in other configurations of deflectable medical devices as well. For example, the illustrated embodiments may find application in medical devices configured for deflection in just one plane.

Figure 2:
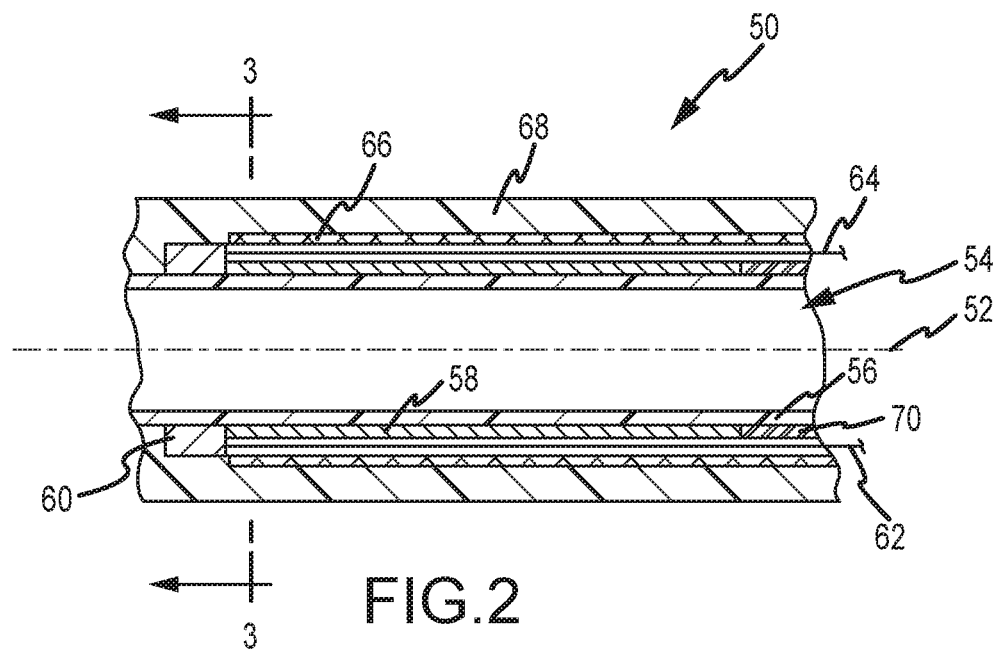
FIG. 2 is a cross-sectional view of a medical device incorporating a strut to reduce axial shortening.

FIG. 2 is an enlarged, cross-sectional view of a deflectable (bendable) distal end portion of a medical device 50, exaggerated to more clearly illustrate aspects of one embodiment of the invention. Without loss of generality, the medical device may comprise a deflectable access sheath 50, which is shown in relation to a longitudinal axis 52. The access sheath 50 may be operably connected to a conventional handle assembly (not shown) or alternatively to a computer-controlled robotic catheter control system (not shown) configured to allow the guiding or steering of the sheath 50 during operation. The sheath 50 includes a relatively large diameter central lumen 54, configured to receive a catheter, fluid delivery devices or other structure or devices as known in the art.

The sheath 50 is shown having an inner tubular liner 56, a strut 58 configured for reducing axial shortening in the deflectable portion of the sheath, a steering or pull ring 60 connected to one or more steering or pull wires 62, 64, a braid layer 66, and an outer polymeric layer 68. Optionally, the sheath 50 may also include a coil 70 (partially shown) extending toward the proximal end portion of the sheath 50, configured to reduce kinking, among other things. Again, without loss of generality, variations are contemplated, for example, where the medical device is an access sheath, a central core component may be the inner liner having a relatively large central lumen, as described above. However, where the medical device is catheter, the central core component may be a catheter shaft.

Figure 3:
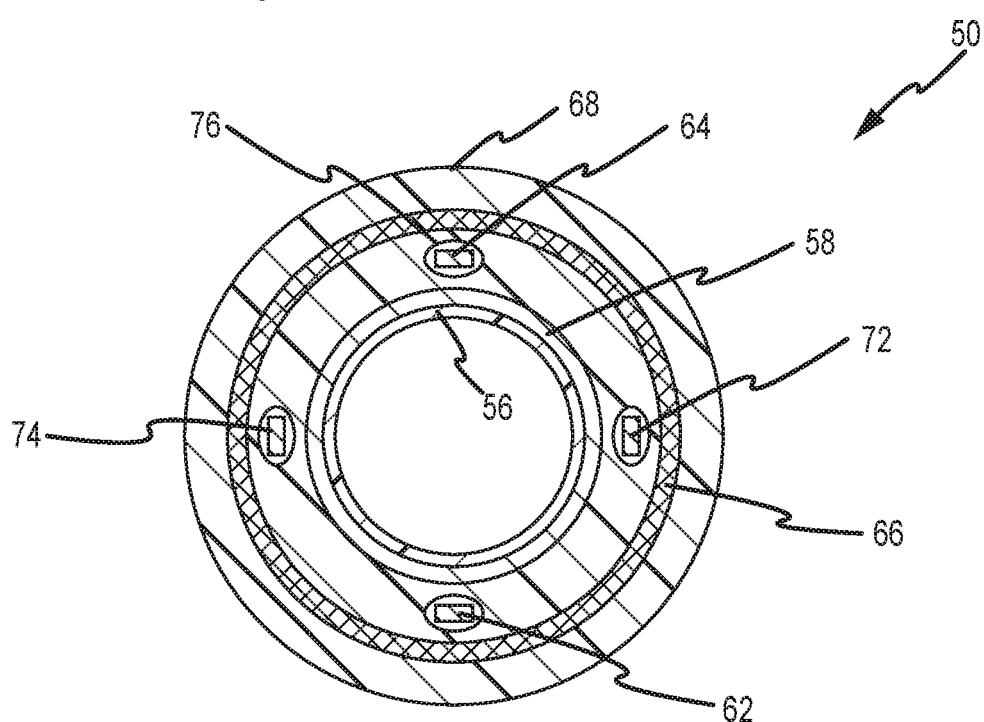
FIG. 3 is a cross-section view of the medical device of FIG. 2 taken substantially along lines 3-3.

FIG. 3 is a cross-sectional view of the sheath 50 of FIG. 2 taken substantially along lines 3-3, and also exaggerated to more clearly illustrate the several components thereof. FIG. 3 shows two further pull wires 72, 74 where each of the four pull wires 62, 64, 72, 74 resides in a lumen formed by a respective tube 76. The wires 62, 64, 72, 74 can act alone (or with other structure) as planarity members.

Referring now to both FIGS. 2 and 3, the inner liner 56 may comprise conventional materials such as polymeric material, and for example only polytetrafluoroethylene (PTFE) material. The inner liner 56 is configured to have an inside diameter of a desired size that defines central lumen 54. The pull ring 60 and associated steering wires 62, 64, 72, 74 may likewise comprise conventional materials and construction approaches, such as stainless steel material for the pull ring and flat (or round) geometry stainless steel wire for the pull wires. The pull wires 62, 64, 72, 74 may also comprise fibrous materials (e.g., KEVLAR®) and can be push members. Further, the braid layer 66 may be configured to hold the pull wires down (i.e., limit radially outwardly going deflections) and may comprise conventional materials and construction approaches, such as for example only metal braid (e.g., 0.002" thick×0.006" wide wire woven in accordance with a known braid pattern). The outer layer 68 may comprise conventional melt processing polymers, such as for example only an elastomer commercially available under the trade designation PEBAX® from Arkema, Inc. of a suitable durometer and melting temperature. The strut 58 may be configured to have an axial length corresponding to the section contemplated to undergo deflection. Constructed embodiments have featured axial lengths in the range between about 1.75" to 2.25", although it should be clearly understood that this length may vary depending on the particular construction details and dimensions of any specific deflectable medical device.

FIGS. 4-15 show various embodiments of strut 58 for use in an access sheath 50 capable of deflection in any radial direction (omni-directional). However, it should be understood that variations are possible, particularly when strut 58 is destined for incorporation into a catheter or deflectable device other than a sheath, destined for incorporation into pre-curved type devices with relatively simple or complex shapes, or destined for a deflectable device with a single plane or two plane deflection range of motion (as described above), rather than for omni-directional deflection.

FIG. 4 is an isometric view of a first embodiment of a strut, designated strut 58a, for incorporation in a deflectable medical device. The strut 58a includes spaced-apart first and second annular end members 78, 80 coupled together by first and second elongate rods 82, 84. The strut 58a is shown in relation to a longitudinal axis 86. In one embodiment, the axis 86 is coincident with the axis 52 of the access sheath 50 (i.e., the strut 58a is coaxially disposed with, for example, the inner liner 56, etc.). In an alternate embodiment, the axis 86 may be offset from the axis 52 of the sheath 50. In a still further alternate embodiment, the strut 58a may have a non-uniform wall thickness.

The first and second annular end members 78, 80 each have central through-bores (best shown in FIG. 3) having respective inside diameters configured to fit over the inner liner 56. The strut 58a has particular advantage in its simplicity of construction. The strut 58a may comprise conventional biocompatible materials relatively impervious to water absorption and having a relatively high modulus of elasticity and as configured suitable for relatively large elastic mechanical strains in view of the contemplated range of deflection, which may typically be between about 90-270 degrees for catheter embodiments and between about 90 and 180 degrees in access sheath embodiments, responsive to typical forces applied to one or more of the pull wires (e.g., between 5-10 pounds, with 6-7 pounds being typical). Such materials may preferably include metal material such as stainless steel or nickel titanium alloys (e.g., superelastic NITINOL), but alternatively may include materials such as polytetrafluoroethylene (PTFE—commercially available TEFLON), polyimide, polyetheretherketones (i.e., PEEK), polyamide (i.e., nylon) or other thermoplastic materials. For example only, stainless steel may have a modulus of elasticity greater than 27 Mpsi, Nitinol may have a modulus of elasticity between about 4-10 Mpsi or greater, while polyimide and polyetheretherketones may have modulus of elasticity around ~0.5 Mpsi.

FIGS. 5-6 are isometric views of a second embodiment of a strut, designated strut 58b, for use in a deflectable medical device. As shown in FIG. 5, the strut 58b is shown in relation to a longitudinal axis 88. In one embodiment, the axis 88 is coincident with the axis 52 of the sheath 50 (i.e., the strut 58b is coaxially disposed with, for example, the inner liner 56, etc.). The strut 58b includes spaced-apart first and second annular end members 90, 92 coupled together by a connecting lattice 94. The first and second annular end members 90, 92 each have central through-bores (shown in FIG. 3) having respective inside diameters (e.g., inside diameter 100 in FIG. 6) configured to fit over the inner liner 56.

As shown in greater detail in FIG. 6, the connecting lattice 94 includes a plurality of spaced-apart helical connecting elements, four such helical elements being incorporated in strut 58b, which are designated helical connecting elements $96_1$, $96_2$, $96_3$ and $96_4$. The plurality of helical connecting elements $96_1$, $96_2$, $96_3$ and $96_4$ intersect at a plurality of flexure nodes $98_1$, $98_2$, . . . , $98_n$. The helical connecting elements $96_1$, $96_2$, $96_3$ and $96_4$ are arranged so that the lattice 94 exhibits a first axial pitch spacing of a first predetermined distance 102, when taken with reference to longitudinally-aligned flexure nodes. As shown, the lattice 94 further exhibits a second axial pitch spacing of a second predetermined distance 104, when taken with respect to adjacent, but circumferentially-offset, flexure nodes. In addition, in the illustrated embodiment, each helical connecting element $96_1$, $96_2$, $96_3$ and $96_4$ has a nominal width, shown as predetermined width 106.

The strut 58b may comprise conventional biocompatible materials relatively impervious to water absorption and having a relatively high modulus of elasticity and as configured suitable for relatively large elastic mechanical strains in view of the contemplated range of deflection, which may typically be between about 90-270 degrees for catheter embodiments and between about 90 and 180 degrees in access sheath embodiments, responsive to typical forces applied to one or more of the pull wires (e.g., between 5-10 pounds, with 6-7 pounds being typical). Such materials may preferably include metal material such as stainless steel or nickel titanium alloys (e.g., superelastic NITINOL), but alternatively may include materials such as polytetrafluoroethylene (PTFE—commercially available TEFLON), polyimide, polyetheretherketones (i.e., PEEK), polyamide (i.e., nylon) or other thermoplastic materials. For example only, stainless steel may have a modulus of elasticity greater than 27 Mpsi, Nitinol may have a modulus of elasticity between about 4-10 Mpsi or greater, while polyimide and polyetheretherketones may have modulus of elasticity around ~0.5 Mpsi.

In one embodiment, the strut 58b was formed using a nickel titanium (NiTi) laser cut tube with an approximate inside diameter (ID) of about 0.025" with a wall thickness of about 0.004". It should be understood that the foregoing is exemplary only, and not limiting in nature, inasmuch as other known approaches for fabrication may be used, other materials may be used and other component dimensions may also be realized.

The strut 58b, due to its symmetrical design, provides substantially uniform resistance to deflection as well as restoration of axial length as taken in any radial direction. The foregoing provides particular advantages in those deflectable medical device embodiments where deflection is contemplated in any radial direction, although as described above, even in single or two plane deflection embodiments, strut 58b would provide for improved planarity, among other things. The overall level of resistance to deflection (i.e., the amount of force needed for deflection) is defined as a function of material, the number of helical elements and the width of each, and the axial pitch between flexure nodes.

FIG. 7 is an isometric view of a third embodiment of a strut, designated strut 58c, for use in a deflectable medical device. The strut 58c is shown in relation to a longitudinal axis 108. The strut 58c includes spaced-apart first and second annular end members 110, 112 coupled together by a connecting lattice 114. The description of strut 58b made above applies in all regards to strut 58c, with the following exception. The lattice 114 includes an increased number of spaced-apart helical connecting elements, for example eight such helical connecting elements as shown, as well as a shortened pitch spacing between flexure nodes. The greater number of helical connecting elements provides a greater immunity to axial shortening (i.e., greater column strength decreases axial shortening). However, the strut 58c, due to its greater rigidity, does present a greater resistance to deflection, thereby also increasing the amount of force needed to achieve a desired deflection amount (e.g., 180-270 degrees).

FIG. 8 is an isometric view of a fourth embodiment of a strut, designated strut 58d, for use in a deflectable medical device. The strut 58d is shown in relation to a longitudinal axis 116. The strut 58d includes spaced-apart first and second annular end members 118, 120 coupled together by a connecting lattice 122. The description of strut 58b made above applies in all regards to strut 58c, with the following exception. The helical connecting elements of the lattice 122 are wider than the predetermined width 106 of the helical connecting elements in strut 58b. While the number of helical connecting elements, and the corresponding pitch spacing are similar to strut 58b, the greater width provides a greater immunity to axial shortening (i.e., greater column strength decreases axial shortening). However, strut 58d, due to its greater rigidity, does present a greater resistance to deflection, thereby also increasing the amount of force needed to achieve a desired deflection amount (e.g., 180-270 degrees).

FIG. 9 is an isometric view of a fifth embodiment of a strut, designated strut 58e, for use in a deflectable medical device. The strut 58e is shown in relation to a longitudinal axis 124. The strut 58e includes spaced-apart first and second annular end members 126, 128 coupled together by a connecting lattice 130. The description of strut 58b made above applies in all regards to strut 58e, with the following exception. The helical connecting elements of the lattice 122 are thinner than the predetermined width 106 of the helical connecting elements of strut 58b. While the number of helical connecting elements, and the corresponding pitch spacing, are similar to that of strut 58b, the reduced helical element width provides a reduction in the amount of force needed to achieve a desired amount of deflection (e.g., 180-270 degrees). However, the thinner helical elements also reduces anti-axial-shortening effectiveness, at least as compared to struts 58b, 58c and 58d.

FIG. 10 is an isometric view of a sixth embodiment of a strut, designated strut 58f. The strut 58f is shown in relation to a longitudinal axis 132. The strut 58f comprises a coil 134 defined by a continuous wire element disposed, for example, in a helix shape between opposing first and second ends 136, 138. In one embodiment, the axis 132 is coincident with the axis 52 of the access sheath 50 (i.e., the strut 58f is coaxially disposed with, for example, the inner liner 56, etc.).

Figure 11:
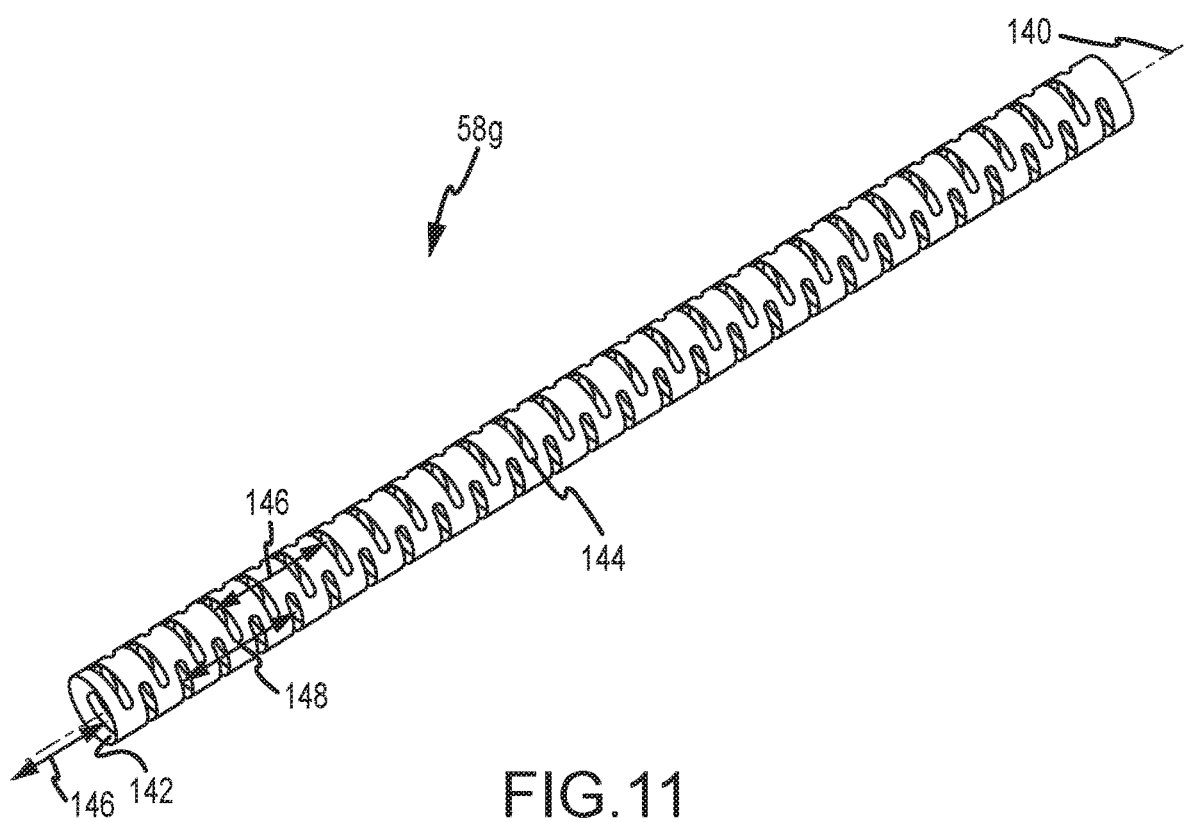
FIG. 11 is an isometric view of a seventh, preferred embodiment of a strut suitable for use in the medical device of FIG. 2.

FIG. 11-14 are views of a seventh, preferred embodiment of a strut, designated strut 58g. FIG. 11 is an isometric view of the strut 58g shown in relation to a longitudinal axis 140. In one embodiment, the axis 140 is coincident with the axis 52 of the sheath 50 (i.e., the strut 58g is coaxially disposed with, for example, the inner liner 56, etc.). The strut 58g comprises a thin-walled tube 142 having a plurality of apertures, for example, slots 144 formed through the wall thickness. Preferably, the slots 144 are circumferentially-oriented (as opposed to axially-oriented). That is, the slot 144 is greater in length in the circumferential direction on the tube than in the longitudinal direction. In the illustrated embodiment, the slots 144 are arranged in a first pair of rows 146. The pair of rows 146 are diametrically-opposing (i.e., 180 degree offset from each other) and longitudinally-extending. In the illustrated embodiment, the slots 144 are further arranged in a second pair of rows 148. The second pair of rows 148 are also diametrically-opposing and longitudinally-extending. Note, only one of the pair of rows 148 is visible in FIG. 11, with the other one of the pair of rows being 180 degrees offset. The slots 144 in each row in the first pair of rows 146 are in registry. Likewise, the slots 144 in each row in the second pair of rows 148 are also in registry. However, the slots 144 in rows 146 are axially offset with the slots 144 in rows 148.

FIG. 12 is a side view of the strut 58g of FIG. 11. The strut 58g includes spaced-apart first and second annular end members 150, 152 and has a predetermined axial length 154.

FIG. 13 is a partial, side view showing in greater detail the encircled distal end portion of the strut 58g. In particular, FIG. 13 is a head on view of the slots 144 formed along one of the pair of rows 148 (only one slot 144 being identified in FIG. 13 for clarity). The slots 144 along the row 148 of slots exhibits a first axial pitch spacing of a first predetermined distance 156. The pitch spacing 156 relates to adjacent slots aligned along a row. As further shown, slots in adjacent rows exhibits a second axial pitch spacing of a second predetermined distance 158. The pitch 158 indicates the axial distance between slots located anywhere around the circumference of the strut. Each of the slots 144 may have a nominal width 160.

The slot 58g may further, optionally, include one or more further apertures, such as axially-extending slots 144a, configured to allow for electrode conductors extending through the core to pass through the strut for electrical connection to a respective electrode. The slots 144a are preferably present in only catheter embodiments with electrodes since for sheath applications, the central lumen must remain clear. While FIG. 13 shows two such slots 144a at a spacing of axial distance 162, the number of slots 144a and respective spacing preferably correspond to the number and spacing of the electrodes in the catheter. Each of the slots 144a has a nominal axial length 164 (excluding radius extensions on each end) and height so that the conductor passing therethrough will not become damaged or otherwise shorted out to the strut. Each of the slots 144a may also offset from the center-line of the circumferentially-extending slot 144 of which they are a part by an offset distance 166.

FIG. 14 is a partial, cross-sectional view of the strut 58g taken substantially along lines 14-14 in FIG. 13. As shown, the first and second annular end members 150, 152 each have central through-bores having respective inside diameters (e.g., inside diameter 168) configured to fit over the outside diameter of the inner liner 56. In addition, the slots are preferably circumferentially extending through a central angle θ with respect to the axis 140.

Figure 15:
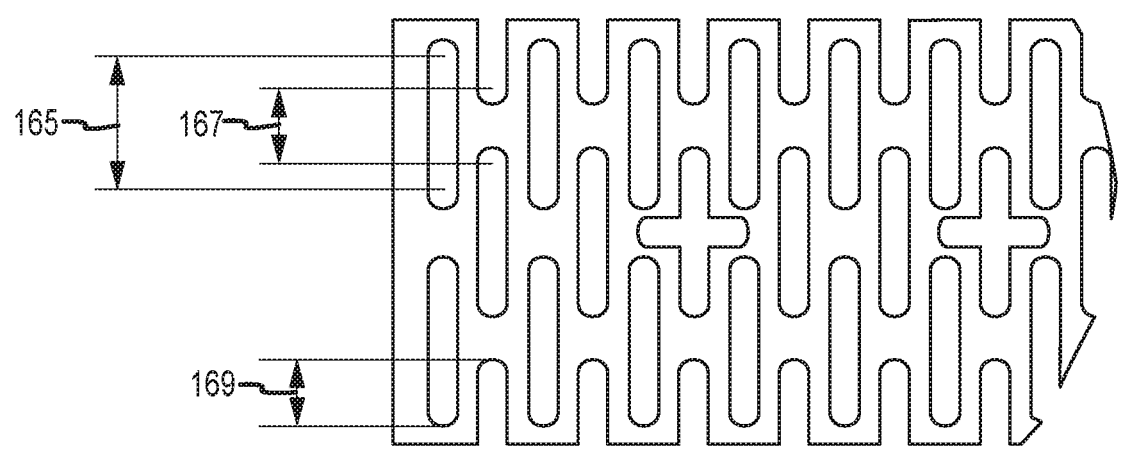
FIG. 15 is an enlarged view showing the strut of FIG. 11 as a flat pattern.

FIG. 15 is an enlarged view of a so-called flat pattern of the strut 58g (i.e., a viewed if the circumference were projected onto a flat surface). As shown, slot 144 may have a predetermined length 165 (excluding end radius—as shown) while slots 144 in the same plane may be separated by a predetermined space 167 (excluding end radius—as shown). Since the strut 58g is configured for omni-directional deflection, the slots 144 in adjacent rows are arranged to have a predetermined minimum amount of overlap 169. The overlap 169 is to provide adequate flexibility in any radial direction. Alternate embodiment, for example, directed to uni-planar or bi-planar deflection, may not necessarily have slot overlap.

The strut 58g may comprise conventional biocompatible materials relatively impervious to water absorption and having a relatively high modulus of elasticity and as configured suitable for relatively large elastic mechanical strains in view of the contemplated range of deflection, which may typically be between about 90-270 degrees for catheter embodiments and between about 90-180 degrees in access sheath embodiments, responsive to typical forces applied to one or more of the pull wires (e.g., between 5-10 pounds, with 6-7 pounds being typical). Such materials may preferably include metal material such as stainless steel or nickel titanium alloys (e.g., superelastic NITINOL), but alternatively may include materials such as polytetrafluoroethylene (PTFE—commercially available TEFLON), polyimide, polyetheretherketones (i.e., PEEK), polyamide (i.e., nylon) or other thermoplastic materials. For example only, stainless steel may have a modulus of elasticity greater than 27 Mpsi, Nitinol may have a modulus of elasticity between about 4-10 Mpsi or greater, while polyimide and polyetheretherketones may have modulus of elasticity around ~0.5 Mpsi.

In one embodiment, the strut 58g may comprise a laser cut tube formed from superelastic nitinol (nickel titanium-NiTi) tubing, straight annealed with an oxide finish. After laser cutting, the tubing may be etched or electro-polished in a straight configuration to remove laser slag and rough edges. An embodiment formed from 0.059" OD superelastic nitinol tubing having nominal 0.004" wall thickness results in the following dimensional configuration: nominal length (i.e., reference numeral 154 in FIG. 12) of 2.25", an inside diameter (i.e., reference numeral 168 in FIG. 14) of 0.053"±0.001", an outside diameter of 0.059"±0.001", a short pitch (i.e., reference numeral 158 in FIG. 13) of 0.022", a long pitch (i.e., reference numeral 156 in FIG. 13) of 0.044", a slot extent (i.e., reference numeral $\theta$ in FIG. 14) of 115 degrees, a slot width of 0.013" typical, a slot length of 0.059" typical (as per flat pattern—see length 165 in FIG. 15), and a slot separation distance of 0.033" typical (as per flat pattern—see distance 167 in FIG. 15).

Another embodiment formed of a laser cut 0.115" outside diameter superelastic nitinol (nickel titanium-NiTi) tubing resulted in the following dimensional configuration: nominal length (i.e., reference numeral 154 in FIG. 12) of 2.10", an inside diameter (i.e., reference numeral 168 in FIG. 14) of 0.107"±0.001", an outside diameter of 0.115"±0.001", a short pitch (i.e., reference numeral 158 in FIG. 13) of 0.033"±0.003", and a slot width of about 0.016"±0.002" typical.

A still further embodiment formed from a 0.133" OD superelastic nitinol (nickel titanium-NiTi) tubing resulted in the following dimensional configuration: nominal length (i.e., reference numeral 154 in FIG. 12) of 2.10", an inside diameter (i.e., reference numeral 168 in FIG. 14) of 0.125"±0.001", an outside diameter of 0.133"±0.001", a short pitch (i.e., reference numeral 158 in FIG. 13) of 0.039"±0.003" and a slot width of 0.019"±0.002" typical.

With reference to FIGS. 2-3 and 16-20, a method of manufacture of a medical device incorporating an embodiment of the strut 58 will now be set forth.

Figure 16:
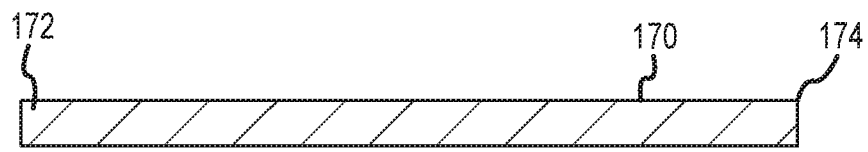
FIGS. 16-20 are isometric side views of a reflow mandrel assembly in various stages of build-up in a method of manufacture of an embodiment of the invention.

FIG. 16 shows a mandrel 170 having a distal end portion 172 and a proximal end portion 174. The mandrel 170 may be circular in radial cross-section and have a desired length, in view of the deflectable medical device to be made.

Figure 17:
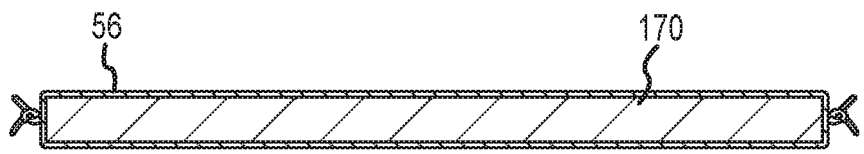

As shown in FIG. 17, the inner liner 56 described above may then be placed on the mandrel 170. Once installed on the mandrel 170, the inner liner 56 may be secured, for example, by knotting one or both ends.

Figure 18:
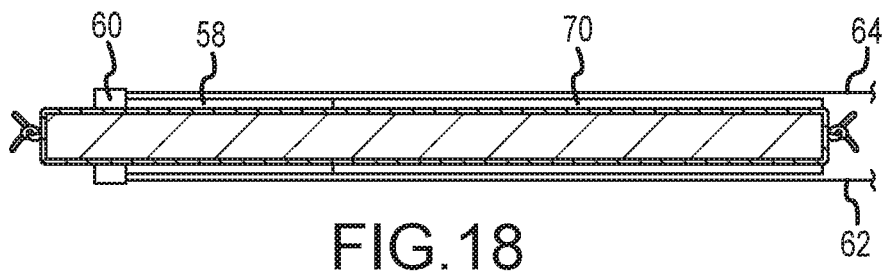

As shown in FIG. 18, the strut 58 is then installed over the liner 56 at the distal end of the mandrel 170 (for embodiments where the distal end portion is the deflectable section of the medical device). In addition, the coil 70 may optionally be installed and butted up against the strut 58 where the coil 70 extends from the proximal end portion of the strut 58 towards the proximal end of the device. The pull ring 60 is then placed on/over the liner 56 butting up to, and on the distal side of the strut 58. The pull wires 62, 64, 72, 74 (enclosed in tubes 76) extend from the pull ring 60 and are placed over the strut 58 (and coil 70, if present), extending in the proximal direction. Note that the strut 58 is directly adjacent the pull ring and extends axially over a length corresponding to the section of the device that will undergo deflection.

Figure 19:

As shown in FIG. 19, the next step may involve placing a sheath layer, such as the braid layer 66, over the pull wires (e.g., to retain outward deflection of the pull wires).

Figure 20:
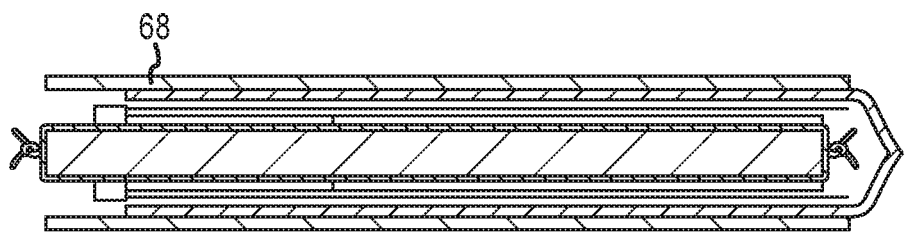

As shown in FIG. 20, the outer layer 68 (e.g., PEBAX material) is then placed over the sub-assembly thus formed. The outer layer 68 may comprise either a single section or alternatively multiple sections of tubing that are either butted together or overlapped with each other. The multiple segments, or layers, of sheath material may be any length and/or hardness (durometer) allowing for flexibility of design, as known in the art.

The assembly thus formed is then subjected to a reflow lamination process, which involves heating the assembly until the outer layer material flows and redistributes around the circumference. The device 50 is then cooled. The distal and proximal end portions of the device 50 may then be finished in a desired fashion.

Generally, except as described above with respect to the various embodiments of the strut 58, the materials and construction methods for manufacture of the access sheath 50 (or catheter in catheter embodiments) may comprise corresponding conventional materials and construction methods, for example only, as seen by reference to U.S. patent application Ser. No. 11/779,488 filed Jul. 18, 2007 entitled CATHETER AND INTRODUCER CATHETER HAVING TORQUE TRANSFER LAYER AND METHOD OF MANUFACTURE, owned by the common assignee of the present invention and hereby incorporated by reference in its entirety.

It should be understood that the foregoing are exemplary only, and not limiting in nature, inasmuch as other known approaches for fabrication may be used, other materials may be used and component dimensions may be realized.

The strut 58g provides substantially uniform resistance to deflection as well as restoration of axial length when taken with respect to a chosen radial direction. In an omnidirectional deflection embodiment, the symmetrical design of the strut 58g for example provides substantially uniform resistance to deflection as well as restoration of axial length when taken in any radial direction. The foregoing provides particular advantages in those deflectable medical device embodiments where deflection is contemplated in any radial direction, although as described above, even in single or two plane deflection, strut 58b would provide for improved planarity, among other things. The overall level of resistance to deflection (i.e., the amount of force needed to achieve a desired amount of deflection) is defined as a function of material, the number of helical elements and the width of each, and the axial pitch between flexure nodes.

For applications directed to the ablative treatment of a cardiac rhythm disorder, such as atrial fibrillation (AF), a catheter system incorporating embodiments of the invention may be combined with either one or both of a positioning/navigation device and/or an electrophysiology mapping device such as the St. Jude Medical EnSite™ Navx system or other systems known in the art, such as positioning systems based on detected magnetic fields (e.g., the Medical Positioning System (gMPS™) of Mediguide Inc., the CARTO navigation and location system of Biosense Webster, Inc., or the AURORA® system of Northern Digital Inc., all of which utilize magnetic fields rather than electrical fields). Use of such positioning, navigation and/or mapping devices may involve fitting the catheter incorporating embodiments of the invention with electrodes and/or magnetic sensors such that such known devices can determine positions and orientations in three-dimensional space and track and navigate such a catheter relative to an EP map or anatomical map or image.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device, comprising:
an elongate core having a proximal end portion and a deflectable distal end portion;
a strut disposed at said distal end portion configured to reduce axial shortening of said deflectable distal end portion of said elongate core due to repeated deflection that would result in a state where said deflectable distal end is compressed relative to an original axial length, said strut having a central through-bore extending longitudinally therethrough, said strut comprising a tube configured for deflection through at least a predetermined range wherein a level of resistance of said strut to deflection is defined as a function of a material of said strut;
a plurality of steering wires configured to deflect said deflectable distal end portion, said steering wires being disposed radially outwardly of said strut;
a steering ring coupled on a distal side of said strut, said steering wires being coupled to said steering ring and extending to said proximal end portion of said elongate core, said steering wires not being coupled with or through said strut; and
a wire mesh defined by a plurality of braided wires, said wire mesh surrounding said steering wires.

2. The device of claim 1 further comprising a coil coupled on a proximal side of said strut wherein said coil and said core are in coaxial relation.

3. The device of claim 1 wherein said braided wires comprise flat braided wires.

4. The device of claim 1 wherein said braided wires comprise metal braided wires.

5. The device of claim 1 wherein said strut comprises first and second annular end members coupled together by first and second elongate rods.

6. The device of claim 1 wherein said strut comprises first and second annular end members coupled together by a lattice including a plurality of spaced helical elements intersecting at a plurality of flexure nodes.

7. The device of claim 6 wherein said lattice includes four helical elements.

8. The device of claim 6 wherein said lattice includes eight helical elements.

9. The device of claim 6 wherein said strut and said core being coupled in coaxial relation.

10. The device of claim 1 wherein said strut comprises a coil defined by a continuous wire element disposed in a helix.

11. The device of claim 1 wherein said strut comprises said tube having a wall with a predetermined wall thickness, said tube having a plurality of slots formed through said wall.

12. The device of claim 11 wherein said slots are circumferentially-oriented.

13. The device of claim 12 wherein said slots are arranged in a first pair of diametrically opposing rows and a second pair of diametrically opposing rows.

14. The device of claim 13 wherein slots in one of said rows of said first pair of diametrically opposing rows are in registry with slots in the other one of said first pair of diametrically opposing rows.

15. The device of claim 13 wherein slots in said first pair of diametrically opposing rows are axially offset from slots in said second pair of diametrically opposing rows.

16. The device of claim 1 wherein said strut comprises said material selected from the group comprising stainless steel, an alloy of nickel and titanium, polyimide, polyamide, PTFE and polyetheretherketones (PEEK).

17. The device of claim 16 wherein said material comprises Nitinol.

18. The device of claim 1 wherein said deflection of said distal end portion ranges between about 90-270 degrees responsive to a pull force between about 5-10 pounds.

19. The device of claim 1 wherein said strut is configured to allow omni-directional deflection of said distal end portion.

20. The device of claim 1 wherein said wire mesh surrounds a portion of said steering wires.

21. The device of claim 1 wherein said steering wires extending to said proximal end portion of said core, being completely outside of said bore over an axial extent of the strut.

22. A medical device, comprising:
an elongate core having a proximal end portion and a deflectable distal end portion;
a strut disposed at said distal end portion configured to reduce axial shortening of said deflectable distal end portion of said elongate core due to repeated deflection that would result in a state where said deflectable distal end is compressed relative to an original axial length, said strut having a central through-bore extending longitudinally therethrough, said strut comprising a tube configured for deflection through at least a predetermined range wherein a level of resistance of said strut to deflection is defined as a function of a material of said strut;

a steering ring coupled on a distal side of said strut;

a plurality of steering wires coupled to said steering ring and extending to said proximal end portion of said core, said steering wires being disposed radially outwardly of said strut, said steering wires being completely outside of said bore over an axial extent of the strut, said steering wires not being coupled with or through said strut; and a wire mesh defined by a plurality of braided wires, said wire mesh surrounding said steering wires.

\* \* \* \* \*